United States Patent [19]

Wijngaarden et al.

[11] Patent Number: 5,162,589
[45] Date of Patent: Nov. 10, 1992

[54] ALKOXYLATION PROCESS CATALYZED BY SODIUM-OR POTASSIUM BARIUM PHOSPHATE

[75] Inventors: Rudolf J. Wijngaarden; Kees Latjes, both of Amsterdam, Netherlands

[73] Assignee: Shell Oil Company, Houston, Tex.

[21] Appl. No.: 895,224

[22] Filed: Jun. 8, 1992

Related U.S. Application Data

[63] Continuation of Ser. No. 769,283, Oct. 1, 1991, abandoned.

[30] Foreign Application Priority Data

Dec. 11, 1990 [GB] United Kingdom ............... 9026832

[51] Int. Cl.$^5$ ................................................ C07C 41/03
[52] U.S. Cl. ................................ 568/618; 568/608; 568/620; 568/45; 568/55; 568/678; 568/679; 560/43; 560/201; 560/250; 560/105; 560/112; 560/240; 564/399; 564/475; 564/505; 530/217; 530/230; 530/232; 554/149
[58] Field of Search ............... 568/618, 608, 620, 45, 568/55, 678, 679; 560/43, 209, 250, 105, 112, 210; 564/399, 475, 505; 530/217, 230, 232; 554/144

[56] References Cited

U.S. PATENT DOCUMENTS

| | | | |
|---|---|---|---|
| 3,752,857 | 8/1973 | Milligan | 260/615 B |
| 4,134,854 | 1/1979 | Milligan | 252/351 |
| 4,210,764 | 7/1980 | Yang et al. | 568/618 |
| 4,223,164 | 9/1980 | Yang et al. | 568/618 |
| 4,239,917 | 12/1980 | Yang | 568/618 |
| 4,302,613 | 11/1981 | Yang et al. | 568/618 |
| 4,306,093 | 12/1981 | Yang et al. | 568/618 |
| 4,453,023 | 6/1984 | McCain et al. | |
| 4,721,817 | 1/1988 | Edwards | |
| 4,967,016 | 10/1990 | Kemp | |

FOREIGN PATENT DOCUMENTS

| | | |
|---|---|---|
| 115084 | 12/1983 | European Pat. Off. |
| 0398450 | 5/1990 | European Pat. Off. |
| 0026544 | 9/1990 | European Pat. Off. |
| 0026546 | 9/1990 | European Pat. Off. |
| 0026547 | 9/1990 | European Pat. Off. |

Primary Examiner—Howard T. Mars

[57] ABSTRACT

Alkylene oxide adducts of organic compounds having active hydrogen atoms are prepared by a process which comprises contacting and reacting an alkylene oxide reactant comprising one or more vicinal alkylene oxides with an active hydrogen containing reactant comprising one or more compounds having active hydrogen atoms in the presence of a catalytically effective amount of sodium barium phosphate or potassium barium phosphate. The product alkoxylates are known to be useful, for instance, as nonionic surfactants, wetting and emulsifying agents, solvent, and chemical intermediates.

14 Claims, No Drawings

ALKOXYLATION PROCESS CATALYZED BY SODIUM-OR POTASSIUM BARIUM PHOSPHATE

This is a continuation of application Ser. No. 769,283, filed Oct. 1, 1991, now abandoned.

FIELD OF THE INVENTION

This invention relates to an alkoxylation process in which one or more alkylene oxides are reacted with one or more compounds having active hydrogen atoms in the presence of a catalytically effective quantity of sodium barium phosphate or potassium barium phosphate. In certain preferred embodiments, the invention relates to processes for the preparation of alkoxylate products having utility as nonionic surfactants.

BACKGROUND OF THE INVENTION

A large variety of products useful, for instance, as nonionic surfactants, wetting and emulsifying agents, solvents, lubricants and chemical intermediates, are prepared by the addition reaction (alkoxylation reaction) of alkylene oxides (epoxides) with organic compounds having one or more active hydrogen atoms. For example, particular mention may be made of the alkanol ethoxylates and alkyl-substituted phenol ethoxylates prepared by the reaction of ethylene oxide with aliphatic alcohols or substituted phenols of 6 to 30 carbon atoms. Such ethoxylates, and to a lesser extent corresponding propoxylates and compounds containing mixed oxyethylene and oxypropylene groups, are widely employed as nonionic detergent components of cleaning formulations for use in industry and in the home. As another example, the addition reaction of propylene oxide with polyols provides intermediates for the preparation of polyurethane products.

An illustration of the preparation of an alkanol ethoxylate (represented by formula III below) by addition of a number (n) of ethylene oxide molecules (formula II) to a single alkanol molecule (formula I) is presented by the equation

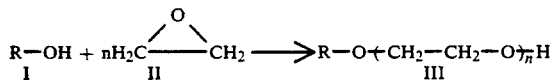

A given alkoxylation process typically results in the production of a mixture of alkoxylate molecules having different numbers of alkylene oxide molecules, e.g., molecules having different values for the adduct number "n" in formula III in the above illustration.

The present invention particularly relates to an alkoxylation process wherein the alkylene oxide addition reaction is catalyzed by sodium barium phosphate, or potassium barium phosphate.

Various compounds of barium and of the other alkaline earth elements are known as alkoxylation catalysts. For instance, it has been reported (e.g., in U.S. Pat. Nos. 3,752,857, 4,134,854, 4,223,164, 4,306,093 and 4,239,917, and in published European Patent Applications 0026544, 0026546, and 0026547) that certain compounds of barium, strontium, and calcium catalyze alkoxylation reactions. U.S. Pat. No. 4,210,764 describes the use of cresylic acids to further promote alkoxylation catalyzed by barium compounds. U.S. Pat. No. 4,302,613 discloses catalyst systems which combine barium and strontium compounds with co-catalysts such as calcium oxide, calcium carbide, calcium hydroxide, magnesium metal, magnesium hydroxide, zinc oxide and aluminum metal.

SUMMARY OF THE INVENTION

Accordingly, the present invention is directed to a process for the preparation of alkylene-oxide adducts of active hydrogen containing organic compounds which comprises contacting and reacting an alkylene oxide reactant comprising one or more vicinal alkylene oxides with an active hydrogen reactant comprising one or more active hydrogen-containing organic compounds, in the presence of a catalytically effective amount of sodium barium phosphate or potassium barium phosphate.

It has been found that an alkoxylation process catalyzed by sodium barium phosphate has benefit in one or more respects over conventional processes catalyzed by other barium compounds.

DESCRIPTION OF THE PREFERRED EMBODIMENTS

In one important respect, the process of this invention provides a product having a distribution of alkylene oxide adducts which is distinguishable from the adduct distribution of products of prior art processes utilizing barium and/or phosphorus containing catalysts. Any alkylene oxide addition reaction produces a mixture of various alkoxylate molecules having different numbers of alkylene oxide adducts (e.g., the alkylene oxide adduct number n in the illustration provided by formula III above). As is known in the art, the distribution of the different alkylene oxide adducts in the product mixture is a factor which in many respects controls the properties of the alkoxylation product, and efforts are made to tailor the distribution of adduct numbers within a product to the product's intended service.

In certain preferred embodiments, the present invention relates to a process characterized by enhanced selectivity for the preparation of particular alkoxylate mixtures, including valuable alkanol alkoxylate mixtures, in which a relatively large proportion of the alkoxylate molecules have a number of alkylene oxide adducts that is within a relatively narrow range of values. For instance, in one such embodiment, the invention is a process for the preparation of ethoxylates of alkanol reactants which comprises contacting an alkanol reactant with an ethoxylate reactant in the presence of an alkoxylation catalyst comprising a catalytically effective amount of an alkali metal barium phosphate selected from sodium barium phosphate, potassium barium phosphate and mixtures thereof. The alkanol ethoxylate product of such a process has an exceptionally narrow ethylene oxide adduct distribution.

The present invention centers upon discoveries associated with the use in an alkoxylation process of a certain class of catalysts. Apart from the use of such catalysts, the process of the invention is, as a general rule, suitably conducted using such reactants and practicing under such processing procedures and reaction conditions as are well known to the art for alkoxylation reactions. Certain preferences may, however, be expressed for particular reactants, procedures and conditions.

Thus, for instance, the invention is preferably applied to processes utilizing an alkylene oxide (epoxide) reactant which comprises one or more vicinal alkylene oxides, particularly the lower alkylene oxides and more particularly those in the $C_2$ to $C_4$ range. In general, the alkylene oxides are represented by the formula

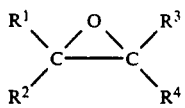

wherein each of the $R^1$, $R^2$, $R^3$ and $R^4$ moieties is individually selected from the group consisting of hydrogen and alkyl moieties. Reactants which comprise ethylene oxide, propylene oxide, or mixtures of ethylene oxide and propylene oxide are more preferred, particularly those which consist essentially of ethylene oxide, or propylene oxide, or their mixtures. Alkylene oxide reactants consisting essentially of ethylene oxide are considered most preferred from the standpoint of commercial opportunities for the practice of alkoxylation processes, and also from the standpoint of benefits to be gained from the use of the invention to prepare products having unique alkylene oxide adduct distributions.

Likewise, the active hydrogen reactants suitably utilized in the process of the invention include those known in the art for reaction with alkylene oxides and conversion to alkoxylate products. Suitable classes of active hydrogen reactants include alcohols, phenols, thiols (mercaptans). amines, polyols, carboxylic acids, and mixtures thereof. Preference generally exists for use of hydroxyl-containing reactants. More preferably, the active hydrogen-containing reactant consists essentially of one or more active hydrogen containing compounds selected from the group consisting of alkanols, alkyl polyols and phenols (including alkyl-substituted phenols).

Among the suitable carboxylic acids, particular mention may be made of the mono- and dicarboxylic acids, both aliphatic (saturated and unsaturated) and aromatic. Specific examples include acetic acid, propionic acid, butyric acid, valeric acid, caproic acid, lauric acid, myristic acid, palmitic acid, steric acid, oleic acid, rosin acids, tall oil acids, terephthalic acid, benzoic acid, phenylacetic acid, toluic acid, acrylic acid, methacrylic acid, crotonic acid and maleic acid.

Among the suitable amines, particular mention may be made of primary, secondary and tertiary alkylamines and of alkylamines containing both amino and hydroxyl groups, e.g., N,N-di(n-butyl)-ethanolamine and tri-propanolamine.

Among the suitable thiols, particular mention may be made of primary, secondary and tertiary alkane thiols having from 1 to 30 carbon atoms, particularly those having from 8 to 20 carbon atoms. Specific examples of suitable tertiary thiols are those having a highly branched carbon chain which are derived via hydrosulfurization of the products of the oligomerization of lower olefins, particularly the dimers, trimers, and tetramers and pentamers of propylene and the butylenes. Secondary thiols are exemplified by the lower alkane thiols, such as 2-propanethiol, 2-butanethiol, and 3-pentanethiols, as well as by the products of the hydrosulfurization of the substantially linear oligomers of ethylene as are produced by the Oxo process. Representative, but by no means limiting, examples of thiols derived from ethylene oligomers include the linear carbon chain products, such as 2-decanethiol, 3-decanethiol, 4-decanethiol, 5-decanethiol, 3-dodecanethiol, 5-dodecanethiol, 2-hexadecanethiol, 5-hexadecanethiol, and 8-octadencanethiol, and the branched carbon chain products, such as 2-methyl-4-tridecanethiol. Primary thiols are typically prepared from terminal olefins by hydrosulfurization under free-radical conditions and include, for example, 1-butanethiol. 1-hexanethiol, 1-dodecanethiol, 1-tetradecanethiol and 2-methyl-1-tridecanethiol.

Among the polyols, particular mention may be made of those having from 2 to 6 hydroxyl groups. Specific examples include the alkylene glycols such as ethylene glycol, propylene glycol, hexylene glycol, and decylene glycol, the polyalkylene glycol ethers, such as diethylene glycol, triethylene glycol, propylene glycol, dipropylene glycol, tripropylene glycol, glycerine and sorbitol.

The alcohols (both mono- and poly-hydroxy) and the phenols (including alkyl-substituted phenols) are preferred classes of active hydrogen reactants for purposes of the invention. Among the phenols, particular mention may be made of phenol and of alkyl-substituted phenols wherein each alkyl substituent has from one to 30 (preferably from one to 20) carbon atoms, for example, p-methylphenol, p-ethylphenol, p-hexylphenol, nonylphenol, p-decylphenol and dodecyl phenol.

Acyclic aliphatic mono-hydric alcohols (alkanols) form a most preferred class of reactants, particularly the primary alkanols, although secondary and tertiary alkanols are also very suitably utilized in the process of the invention. Preference can also be expressed, for reason of both process performance and commercial value of the product, for alkanols having from one to 30 carbon atoms, with $C_6$ to $C_{24}$ alkanols considered more preferred and $C_8$ to $C_{20}$ alkanols considered most preferred. As a general rule, the alkanols may be of branched or straight chain structure, although preference further exists for alkanol reactants in which greater than 50 per cent, more preferably greater than 60 per cent and most preferably greater than 70 per cent of the molecules are of linear (straight-chain) carbon structure.

The general suitability of such alkanols as reactants in alkoxylation reactions is well recognized in the art. Commercially available mixtures of primary monohydric alkanols prepared via the oligomerization of ethylene and the hydroformylation or oxidation and hydrolysis of the resulting higher olefins are particularly preferred.

The active hydrogen containing reactant is also very suitably the alkoxylate product of a previous alkoxylation of an active hydrogen containing compound. Thus, for example, advantages associated with the invention can be realized by applying the invention to further ethoxylate an alkanol ethoxylate which has previously been prepared by ethoxylation of an alkanol ethoxylate.

In general terms, for purposes of the invention, the alkylene oxide reactant and the active hydrogen reactant are necessarily contacted in the presence of a catalytically effective amount of sodium- or potassium barium phosphate, that is, an amount sufficient to positively influence the activity and/or the selectivity of the alkoxylation reaction.

It is critical to the invention that the catalyst comprise a catalytically effective amount of the specific sodium barium phosphate or potassium barium phosphate. For purposes of this specification sodium barium phosphate means the compound of the formula $NaBaPO_4$.

Sodium barium phosphate may be suitably synthesized by neutralization of phosphoric acid with barium hydroxide (mol ratio 1:1) and followed by addition of at least 1 mol of sodium hydroxide to the resulting neutralized mixture.

Sodium barium phosphate or potassium barium phosphate is present in a catalytically-effective amount in the alkoxylation reaction mixture of the process of the invention, that is, in an amount which has a meaningful influence upon alkoxylation reaction activity and/or selectivity. Preferred for practice of the invention is a quantity of phosphate which is at least about 0.1% w (per cent by weight), calculated on the weight of the active hydrogen containing reactant. More preferred is the use of the catalyst in a quantity which is between about 0.2 and 5% w, while a quantity of catalyst in the range from about 0.5 to 2% w is considered most preferred, particularly for processes involving mono-hydric alkanol and ethylene oxide reactants. Substantially greater quantities of catalyst are also suitable, for instance up to 10% w, calculated on active hydrogen reactant. As a rule, the higher the desired average alkylene oxide adduct number of the alkoxylate product and the higher the desired rate of reaction, the greater the required quantity of catalyst.

The catalyst, as well as the reactants, are preferably substantially free of water. In a preferred mode of practice of the invention, water is removed from a mixture of active hydrogen reactant and catalyst, by heating under vacuum prior to contact with alkylene oxide reactant.

In terms of processing procedures, the alkoxylation reaction in the invention may be conducted in a generally conventional manner. For example, the catalyst may initially be mixed with liquid active hydrogen reactant. The mixture of catalyst and liquid reactant is contacted, preferably under agitation, with alkylene oxide reactant, which is typically introduced in gaseous form, at least for the lower alkylene oxides. The order in which the reactants and catalyst are contacted has not been found to be critical to the invention.

While these procedures describe a batch mode of operation, the invention is equally applicable to a continuous process.

The catalyst may be either soluble (either partially or completely) or insoluble in this liquid reactant as well as in liquid mixtures of the reactant and the product formed as the process is carried out.

Overall, the two reactants are utilized in quantities which are predetermined to yield an alkoxylate product of the desired mean or average adduct number. The average adduct number of the product is not critical to this process. Such products commonly have an average adduct number in the range from less than one to 30 or greater, although the invention is also suitable for alkoxylation of reactants, such as polyols, for which substantially higher average adduct number products are often desired. In particularly preferred embodiments, the invention is applied for the manufacture of ethylene oxide adducts of primary mono-hydric alkanols in the carbon number range from 6 to 24, having an average of between 1 to 15. more preferably between 2 and 12, oxyethylene groups per ethoxylate molecule, and characterized by very desirable adduct distribution.

In general terms, suitable and preferred process temperatures and pressures for purposes of this invention are the same as in conventional alkoxylation reactions between the same reactants, employing conventional catalysts. A temperature of at least 90° C., particularly at least 120° C. and most particularly at least 130° C., is typically preferred from the standpoint of the rate of reaction, while a temperature less than 250° C. particularly less than 210° C., and most particularly less than 190° C., is typically desirable to minimize degradation of the product. As is known in the art, the process temperature can be optimized for given reactants, taking such factors into account.

Superatmospheric pressures, e.g., pressures between 0.7 and 11 barg, are preferred, with pressure being sufficient to maintain the active hydrogen reactant substantially in the liquid state.

When the active hydrogen reactant is a liquid and the alkylene oxide reactant is a vapor, alkoxylation is then suitably conducted by introducing alkylene oxide into a pressure reactor containing the liquid active hydrogen reactant and the catalyst. For considerations of process safety, the partial pressure of a lower alkylene oxide reactant is preferably limited, for instance, to less than 4 bar, and/or the reactant is preferably diluted with an inert gas such as nitrogen, for instance, to a vapor phase concentration of 50 per cent or less. The reaction can, however, be safely accomplished at greater alkylene oxide concentration, greater total pressure and greater partial pressure of alkylene oxide if suitable precautions, known to the art, are taken to manage the risks of explosion. A total pressure of between 3 and 7 barg, with an alkylene oxide partial pressure between 1 and 4 barg, is particularly preferred, while a total pressure of between 3.5 and 6.5 barg, with an alkylene oxide partial pressure between 1.5 and 3.5 barg, is considered more preferred.

The time required to complete a process according to the invention is dependent both upon the degree of alkoxylation that is desired (i.e., upon the average alkylene oxide adduct number of the product) as well as upon the rate of the alkoxylation reaction (which is, in turn dependent upon temperature, catalyst quantity and nature of the reactants). A typical reaction time for preferred embodiments is in the range from 1 to 24 hours.

After the ethoxylation reaction has been completed, the product is preferably cooled. If desired, catalyst can be removed from the final product, although catalyst removal is not necessary to the process of the invention. Catalyst residues may be removed, for example, by filtration, centrifugation, extraction, or the like. The fact that a high degree of removal of catalyst residues can be accomplished by physical means suggests that the active catalyst species is essentially insoluble in the reaction mixture.

In certain preferred embodiments, the level of catalyst residues and in some cases the quantity of by-products in the reaction product are reduced by treatment of the alkoxylation reaction product with a material selected from the group consisting of strong acids (particularly oxalic acid and/or phosphoric acid), alkali metal carbonates and bicarbonates, solid organic acids, zeolites (particularly Y zeolite and mordenite), and clays. The products are contacted with one or more of such materials and then filtered, preferably at elevated temperature, e.g., 100° C. An aqueous wash of the product at a temperature of about 125° C. has also been found to be particularly useful for removal of catalyst residues and by-products.

The process of the invention may be applied to the preparation of products having very desirable alkylene oxide adduct distributions, and, in many cases, products for which the adduct distribution differs substantially from that produced by related prior art alkoxylation catalysts. In addition, the process produces a product having a relatively low content of unreacted (residual) active hydrogen reactant, that is a relatively low content of material for which the adduct number is zero. A high level of residual reactant either represents a loss of valuable reactant, or requires that further processing of the product be carried out to recover the reactant. Moreover, the presence of the unreacted material is often of disadvantage from the standpoint of product quality and environmental concerns. For instance, residual alkanol in a detergent alcohol ethoxylate product contributes to volatile organic emissions during spray drying of detergent formulations. Still further, the process of the invention is capable of providing a product having a relatively low content of polyalkylene glycols and other by-products. Moreover, the polyalkylene glycol by-products which do result from practice of this invention are generally of a relatively high carbon number than the by-products of conventional alkoxylation processes, and are more readily separated from the principal alkoxylation products by physical means such as filtration, centrifugation, and the like.

EXAMPLE 1

Preparation of Sodium Barium Phosphate

To 585.4 g of water was added in the following order (a) 148.7 g of potassium hydroxide, (b) 244.2 g of the disodium salt of ethylene diamine tetracetic acid ($2H_2O$) and (c) 206.9 g of barium hydroxide ($8H_2O$). A clear solution was obtained. To this solution was added 214.2 g of 20% by weight aqueous phosphoric acid. 131.6 g of solid precipitated from the mixture and was collected by filtration. The solid was analyzed by X-ray powder diffraction and found to be $NaBaPO_4$.

EXAMPLE 2

Preparation of Sodium Barium Phosphate

To a 20% by weight phosphoric acid solution in water (containing 100 g $H_3PO_4$) were added solid barium hydroxide ($Ba(OH)_2.8H_2O$) in a mol ratio of 1:1 and solid sodium hydroxide (2 mol per 1 mol phosphoric acid). The mixture was stirred for 5 minutes. A white precipitate was formed, which was filtered off and dried. The solid was analyzed by X-ray powder diffraction and elemental analysis and was found to be $NaBaPO_4.9H_2O$. The yield was 100% on phosphoric acid intake.

EXAMPLE 3

Preparation of the Ethoxylate of DOBANOL-1 ($C_{11}H_{23}OH$)

DOBANOL is a registered trademark of Shell International Chemical Company.

To a 5-liter autoclave were introduced 1000 g of DOBANOL-1 and 20 g of $NaBaPO_4$. The mixture was kept under a nitrogen atmosphere and stirred at about 750 rpm, while the temperature in the autoclave was raised to 155° C. Ethylene oxide was then introduced into the autoclave at a pressure of 4 bar. The nitrogen partial pressure was maintained at 2.5 bar, so that the gas cap contained always less than 40% ethylene oxide.

The reaction was continued until 1.8 kg of ethylene oxide had reacted with 1 kg of DOBANOL-1. During the batch the volume of the liquid increased from 20% to 70% of the total reactor volume. After 2.5 hours the reaction was complete.

After the ethylene oxide gas stream was discontinued the autoclave was kept at a temperature of 155° C. for 30 min. Thereafter the reaction mixture was cooled to 60° C. and kept under a nitrogen stream for 15 min.

The ethylene oxide adduct distribution of the product is presented in the following table:

| Adduct Number | Concentration |
| --- | --- |
| 0 | 6.1% w |
| 1 | 0.8% w |
| 2 | 2.3% w |
| 3 | 4.6% w |
| 4 | 8.2% w |
| 5 | 14.8% w |
| 6 | 17.2% w |
| 7 | 17.2% w |
| 8 | 13.7% w |
| 9 | 8.6% w |
| 10 | 4.3% w |
| 11 | 1.7% w |
| 12 | 0.6% w |
| 13 | 0.1% w |
| 14 | 0.0% w |
| 15 | 0.0% w |

$NaBaPO_4$ is also catalytically active in the alkoxylation reaction when it is in situ formed as well as when it contains $H_2O$, e.g. $9H_2O$.

What is claimed is:

1. A process for the preparation of alkylene oxide adducts of active hydrogen containing organic compounds, which comprises contacting and reacting an alkylene oxide reactant comprising one or more vicinal alkylene oxides with an active hydrogen containing reactant comprising one or more active hydrogen containing organic compounds, in the presence of a catalytically effective amount of an alkali metal barium phosphate selected from the group consisting of sodium barium phosphate, potassium barium phosphate and mixtures thereof.

2. The process as claimed in claim 1, wherein the alkylene oxide reactant consists essentially of one or more alkylene oxides selected from the group consisting of ethylene oxide and propylene oxide.

3. The process as claimed in claim 2, wherein the active hydrogen containing reactant consists essentially of one or more compounds selected from the group consisting of alcohols, phenols and polyols.

4. The process as claimed in claim 3, wherein the active hydrogen containing reactant consists essentially of one or more active hydrogen containing compounds selected from the group consisting of alkanols having from one to 30 carbon atoms and alkyl-substituted phenols wherein each alkyl substituent has from one to 30 carbon atoms.

5. The process as claimed in claim 4, wherein the active hydrogen containing reactant consists essentially of one or more $C_1$–$C_{30}$ primary mono-hydric alkanols.

6. The process as claimed in claim 5, wherein the active hydrogen containing reactant consists essentially of primary mono-hydric alkanols having carbon numbers in the range from 6 to 24, inclusive.

7. The process as claimed in claim 6, wherein the active hydrogen containing reactant consists essentially of primary mono-hydric alkanols having carbon numbers in the range from 8 to 20, inclusive.

8. The process as claimed in claim 7, wherein greater than 50% of the molecules of the primary mono-hydric alkanols are of linear carbon structure.

9. The process as claimed in claim 8, wherein greater than 70% of the molecules are of linear carbon structure.

10. The process as claimed in claim 1 wherein said alkali metal barium phosphate is sodium barium phosphate.

11. The process as claimed in claim 10, wherein the sodium barium phosphate is present in an amount between 0.2 and 5 per cent by weight, calculated on the weight of active hydrogen-containing reactant.

12. The process as claimed in claim 1, wherein said alkali metal barium phosphate is potassium barium phosphate.

13. The process as claimed in claim 12, wherein the potassium barium phosphate is present in an amount between 0.2 and 5 percent by weight, calculated on the weight of active hydrogen-containing reactant.

14. The process as claimed in claim 1, wherein the temperature is in the range of from 90° C. to 250° C., preferably from 130° C. to 190° C.

* * * * *